US012670590B2

(12) United States Patent
Wang

(10) Patent No.: US 12,670,590 B2
(45) Date of Patent: Jun. 30, 2026

(54) AUTOMATED DETECTION OF CHOROIDAL NEOVASCULARIZATION (CNV)

(71) Applicant: Genentech, Inc., South San Francisco, CA (US)

(72) Inventor: Xiaoyong Wang, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 272 days.

(21) Appl. No.: 18/328,442

(22) Filed: Jun. 2, 2023

(65) Prior Publication Data

US 2023/0394658 A1 Dec. 7, 2023

Related U.S. Application Data

(63) Continuation of application No. PCT/US2021/061562, filed on Dec. 2, 2021.

(Continued)

(51) Int. Cl.
*G06T 7/00* (2017.01)
*A61B 3/00* (2006.01)
(Continued)

(52) U.S. Cl.
CPC .......... *G06T 7/0012* (2013.01); *A61B 3/0025* (2013.01); *A61B 3/102* (2013.01);
(Continued)

(58) Field of Classification Search
CPC .................... G06T 7/0012; G06T 7/11; G06T 2207/10101; G06T 2207/20084; G06T 2207/20132; G06T 2207/30041; G06T 2207/30132; A61B 3/0025; A61B 3/102; A61B 3/1225; G16H 50/20; G06V 10/255
See application file for complete search history.

(56) References Cited

U.S. PATENT DOCUMENTS

2016/0278627 A1   9/2016  Huang et al.
2019/0108636 A1*  4/2019  Bagherinia ......... G06F 18/2415
2020/0033431 A1   1/2020  Schlemper et al.

FOREIGN PATENT DOCUMENTS

CN      103841991 A     6/2014
CN      104768446 A     7/2015
(Continued)

OTHER PUBLICATIONS

Sun, Zhongyang, and Yankui Sun. "Automatic detection of retinal regions using fully convolutional networks for diagnosis of abnormal maculae in optical coherence tomography images." Journal of biomedical optics 24.5 (2019): 056003-056003. (Year: 2019).*

(Continued)

*Primary Examiner* — Oneal R Mistry
*Assistant Examiner* — Rachel L Roberts
(74) *Attorney, Agent, or Firm* — Haynes and Boone, LLP

(57) ABSTRACT

A method and system for detecting an advanced stage of age-related macular degeneration in a retina. Optical coherence tomography (OCT) imaging data for a retina is received. A presence of choroidal neovascularization (CNV) in the retina is detected, via a machine learning system, using the OCT imaging data. An output that indicates that the presence of CNV in the retina has been detected is generated.

20 Claims, 7 Drawing Sheets

Related U.S. Application Data

(60) Provisional application No. 63/121,723, filed on Dec. 4, 2020.

(51) Int. Cl.

| | | |
|---|---|---|
| *A61B 3/10* | (2006.01) | |
| *A61B 3/12* | (2006.01) | |
| *G06T 7/11* | (2017.01) | |
| *G16H 50/20* | (2018.01) | |

(52) U.S. Cl.
CPC .............. *A61B 3/1225* (2013.01); *G06T 7/11* (2017.01); *G16H 50/20* (2018.01); *G06T 2207/10101* (2013.01); *G06T 2207/20084* (2013.01); *G06T 2207/20132* (2013.01); *G06T 2207/30041* (2013.01)

(56) References Cited

FOREIGN PATENT DOCUMENTS

| | | | | | |
|---|---|---|---|---|---|
| CN | 111340789 A | * | 6/2020 | ............. | G06N 3/045 |
| JP | 2013518695 A | | 5/2013 | | |
| JP | 2019209136 A | | 12/2019 | | |
| WO | 2014074178 A1 | | 5/2014 | | |
| WO | WO-2018069768 A2 | * | 4/2018 | ............... | A61B 3/12 |
| WO | WO-2019210079 A1 | * | 10/2019 | ........... | G06T 7/0012 |

OTHER PUBLICATIONS

International Search Report and Written Opinion mailed Mar. 16, 2022 in International Application No. PCT/US2021/061562, 11 pages.

International Preliminary Report on Patentability issued May 30, 2023 in International Application No. PCT/US2021/061562, 7 pages.

Prove, "Squeeze-and-Excitation Networks. Setting a New State of the Art on ImageNet." Published in Towards Data Science. Oct. 17, 2017, pp. 1-5.

Salinas-Alaman et al., "Using Optical Coherence Tomography to Monitor Photodynamic Therapy in Age Related Macular Degeneration", American Journal of Ophthalmology, Elsevier, Amsterdam, Netherlands. Jul. 1, 2005, pp. 23-28, vol. 140, No. 1.

Sikorski et al., "Drusen with Accompanying Fluid underneath the Sensory Retina", American Academy of Ophthalmology, Jan. 1, 2011, pp. 82-92, vol. 118, No. 1.

Sayanagi et al., "Comparison of Spectral-Domain versus Time-Domain Optical Coherence Tomography in Management of Age-Related Macular Degeneration with Ranibizumab", American Academy of Ophthalmology, May 1, 2009, pp. 947-955, vol. 116, No. 5.

Office Action dated Jul. 25, 2025 from corresponding Chinese Application No. 2021800816484, original and translation, 27 pages.

Lee et al., al."SRM: A Style-based Recalibration Module for Convolutional Neural Networks", Mar. 26, 2019, arXiv: 1903.10829, 11 pages.

Office Action mailed Oct. 7, 2025 in related Japanese application No. 2023-533849, 4 pages.

* cited by examiner

200

RECEIVE OPTICAL COHERENCE TOMOGRAPHY
(OCT) IMAGING DATA FOR A RETINA
202

DETECT, VIA A MACHINE LEARNING SYSTEM, A
PRESENCE OF CHOROIDAL
NEOVASCULARIZATION (CNV) IN THE RETINA
USING THE OCT IMAGING DATA
204

GENERATE AN OUTPUT THAT INDICATES THAT
THE PRESENCE OF CNV IN THE RETINA HAS
BEEN DETECTED
206

300

RECEIVE OPTICAL COHERENCE TOMOGRAPHY
(OCT) IMAGING DATA FOR A RETINA
302

PREPROCESS THE OCT IMAGING DATA TO
FORM AN OCT INPUT
304

DETECT, VIA A MACHINE LEARNING SYSTEM,
A PRESENCE OF CHOROIDAL
NEOVASCULARIZATION (CNV) IN THE RETINA
USING THE OCT INPUT
306

400

RECEIVE OPTICAL COHERENCE TOMOGRAPHY
(OCT) IMAGING DATA FOR A PATIENT EYE
402

COLLAPSE THE OCT IMAGING DATA ABOUT A
REGION OF INTEREST, TO FORM AN OCT INPUT
404

ANALYZE THE OCT INPUT FOR A PRESENCE
OF CHOROIDAL NEOVASCULARIZATION (CNV)
DISEASE
406

DETECT THE PRESENCE OF CNV DISEASE IN
THE PATIENT EYE USING THE OCT INPUT
408

500

AUTOMATED DETECTION OF CHOROIDAL NEOVASCULARIZATION (CNV)

CROSS-REFERENCE TO RELATED APPLICATIONS

The present application is a continuation of International Application No. PCT/US2021/061562, filed Dec. 2, 2021, which claims priority to and the benefit of the U.S. Provisional Patent Application No. 63/121,723, filed Dec. 4, 2020, titled "Automated Detection Of Choroidal Neovascularization (CNV)," which are hereby incorporated by reference in their entirety as if fully set forth below and for all applicable purposes.

FIELD

This application relates to the detection of choroidal neovascularization (CNV), and more particularly, to automated detection of CNV in an eye using optical coherence tomography (OCT) imaging data.

INTRODUCTION

Age-related macular degeneration (AMD) is a leading cause of vision loss in subjects 50 years and older. Some subjects with AMD can develop choroidal neovascularization (CNV), in which new, abnormal blood vessels originating in the choroid layer of the eye grow into the retina and leak fluid from the blood into the retina. Upon entering the retina, the fluid may distort the vision of a subject immediately. Over time, the fluid can damage the retina itself, for example, by causing the loss of photoreceptors in the retina. Unfortunately, there are currently no ways to anticipate the development of CNV. Accordingly, a desire exists for ways to detect and track the progression of CNV.

SUMMARY

In one or more embodiments, a method is provided for detecting an advanced stage of age-related macular degeneration. Optical coherence tomography (OCT) imaging data for a retina is received. A presence of choroidal neovascularization (CNV) in the retina is detected, via a machine learning system, using the OCT imaging data.

In one or more embodiments, a method is provided for detecting an advanced stage of age-related macular degeneration. Optical coherence tomography (OCT) imaging data is received for a retina. The OCT imaging data is preprocessed to form an OCT input. A presence of choroidal neovascularization (CNV) in the retina is detected, via a machine learning system, using the OCT input.

BRIEF DESCRIPTION OF THE DRAWINGS

For a more complete understanding of the principles disclosed herein, and the advantages thereof, reference is now made to the following descriptions taken in conjunction with the accompanying drawings, in which.

Figure 1:
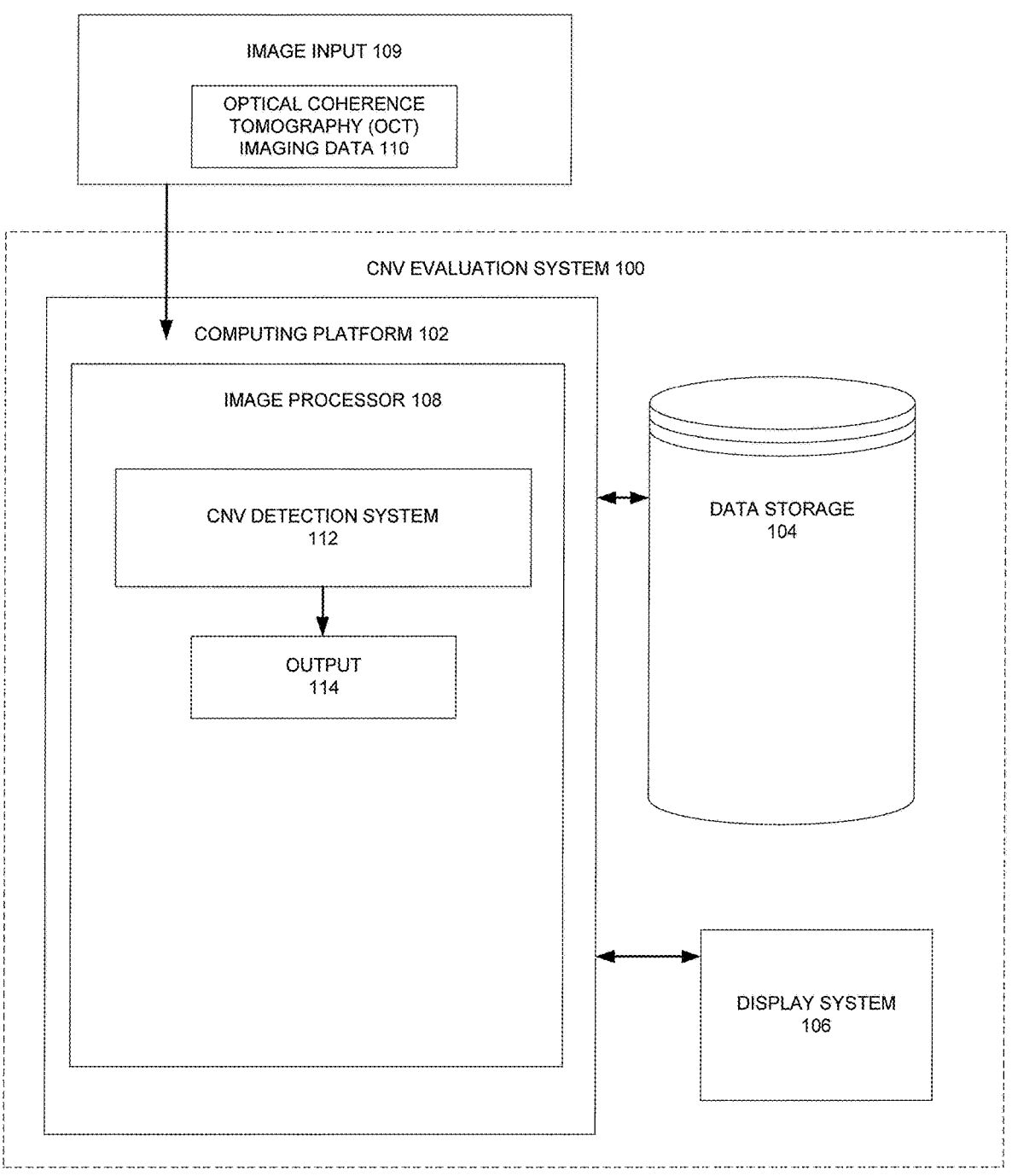
FIG. 1 is a block diagram of a choroidal neovascularization (CNV) detection system in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

I. Overview

Age-related macular degeneration (AMD) is an eye disease that can blur a subject's central vision and occurs when aging causes damage to portions of the retina, such as the macula. AMD can be in dry form (often referred to as atrophic AMD) or wet AMD (often referred to advanced neovascular AMD). Wet AMD occurs due to growth of abnormal blood vessels in the eye. These new blood vessels, which originate from the choroid, often leak fluid (e.g., fluid from blood or red blood cells), wetting the retina and eventually damaging portions of the retina, such as the macula. This condition is often referred to as choroidal neovascularization (CNV), which can result from, not only AMD, but also other causes such as, for example, pathologic myopia, ocular histoplasmosis, eye trauma (e.g., angioid streaks), lacquer cracks, and uvetis (severe ocular inflammation).

Detecting CNV may be important to generating a personalized treatment regimen for a subject, mitigating retinal damage, and understanding a subject's AMD pathogenesis. Detecting CNV can involve use of multiple methods, including Optical Coherence Tomography (OCT), Fluorescein, ICG Angiography, and observed reduced visual acuity by a medical professional. OCT, in particular, is an imaging technique in which light is directed at a biological sample (e.g., biological tissue) and the light that is reflected from features of that biological sample is collected to capture two-dimensional or three-dimensional, high-resolution cross-sectional images of the biological sample.

It is generally recognized that fluid associated with the retina (e.g., intraretinal fluid, subretinal fluid, subretinal pigment epithelial fluid, etc.) may be an accurate and reliable indicator of CNV. Thus, a methodology for accurately and reliably detecting this fluid can serve as an accurate and reliable indicator of CNV. OCT images enable visualizing such fluid and therefore, the presence of fluid in an OCT image of a subject may be used as an indicator of CNV in the retina of the subject. However, manual analysis of OCT images by human graders may be time-consuming and prone to error. Thus, methods and systems that can automate the detection of CNV using OCT imaging data are desirable.

The present embodiments aim to leverage beneficial characteristics of OCT imaging data in efforts to improve detection of CNV disease. In particular, the present embodiments include artificial intelligence (AI), and in particular machine learning and deep learning systems, that automatically analyze OCT imaging data and classify CNV disease based on the analyzed OCT imaging data. These learning systems can classify CNV disease at least as accurately as manual analysis, yet provide analyses more quickly and more cost-effectively than current methods, especially when processing large datasets. Moreover, analyses and diagnoses using learning systems enable the retaining of previous data within the learning systems and a folding back in of such data to perpetually increase the accuracy and speed of the automated CNV analysis and permit forward predictions of CNV progression. Thus, the methods and systems of the present disclosure allow for improved and automated analysis of OCT imaging data using a learning system (e.g., a neural network system) for the detection of CNV disease.

The present disclosure provides systems and methods of automated detection of CNV disease in a patient eye using OCT imaging data. In one embodiment, for example, the present disclosure provides systems and methods of analyzing OCT imaging data using a neural network system. That is, for example, neural network systems may receive OCT imaging data and generate CNV disease classification results that may be more accurate and informative compared to manual detection or even detection using static algorithms. This may be because using neural network systems are trained to constantly optimize parameters of interest, thus improving detection accuracy. Moreover, modules and/or blocks can be added, removed or manipulated within the network to focus analysis to key portions of the OCT imaging data, to incorporate loss function, to augment OCT imaging data (through e.g., rotation, translation, and flipping), to reduce model size for e.g., speed, and automatically recalibrate channel-wise feature response.

The neural network system may include but not limited to a convolutional neural network (CNN) system, deep learning system (e.g., U-Net deep learning neural network, Y-Net deep learning neural network, etc.), and/or the like. As discussed above, such systems and methods that utilize neural network systems for analyzing OCT images facilitate accurate detection of CNV disease while regularly allowing for consistent improvement in the analysis accuracy over time through reincorporation of said results back into the neural network system.

For example, OCT imaging data can be pre-processed, using a neural network system, by collapsing the data about a specific region of interest, such as the retinal pigment epithelium layer on the eye. Collapsing the OCT imaging data about a region of interest includes collapsing the OCT imaging data about a retinal pigment epithelium (RPE) layer of the patient eye, flattening one or more OCT images towards the RPE layer, and/or cropping a number of pixels about the RPE layer. This, combined with analysis of specific portions of the OCT imaging data (e.g., central B-scans), allows for increased focused analysis of the OCT data as well as reduced processing power needed for the analysis, therefore reducing analysis timing.

Recognizing and taking into account the importance and utility of a methodology and system that can provide the improvements described above, the specification describes various embodiments for automated detection of CNV using OCT imaging data. More particularly, the specification describes various embodiments of methods and systems for accurately and reliably detecting CNV in a retina using OCT imaging data and a machine learning system (e.g., a neural network system).

II. Definitions

The disclosure is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion.

In addition, as the terms "on," "attached to," "connected to," "coupled to," or similar words are used herein, one element (e.g., a component, a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

The term "subject" may refer to a subject of a clinical trial, a person undergoing treatment, a person undergoing anti-cancer therapies, a person being monitored for remission or recovery, a person undergoing a preventative health analysis (e.g., due to their medical history), or any other person or subject of interest. In various cases, "subject" and "patient" may be used interchangeably herein.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, chemistry, biochemistry, molecular biology, pharmacology and toxicology are described herein are those well-known and commonly used in the art.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "about" used with respect to numerical values or parameters or characteristics that can be expressed as numerical values means within ten percent of the numerical values. For example, "about 50" means a value in the range from 45 to 55, inclusive.

The term "ones" means more than one.

As used herein, the term "plurality" can be 2, 3, 4, 5, 6, 7, 8, 9, 10, or more.

As used herein, the term "set of" means one or more. For example, a set of items includes one or more items.

As used herein, the phrase "at least one of," when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required. For example, without limitation, "at least one of item A, item B, or item C" means item A; item A and item B; item B; item A, item B, and item C; item B and item C; or item A and C. In some cases, "at least one of item A, item B, or item C" means, but is not limited to, two of item A, one of item B, and ten of item C; four of item B and seven of item C; or some other suitable combination.

As used herein, a "model" may include one or more algorithms, one or more mathematical techniques, one or more machine learning algorithms, or a combination thereof.

As used herein, "machine learning" includes the practice of using algorithms to parse data, learn from it, and then make a determination or prediction about something in the world. Machine learning uses algorithms that can learn from data without relying on rules-based programming.

As used herein, an "artificial neural network" or "neural network" (NN) may refer to mathematical algorithms or computational models that mimic an interconnected group of artificial neurons that processes information based on a connectionistic approach to computation. Neural networks, which may also be referred to as neural nets, can employ one or more layers of linear units, nonlinear units, or both to predict an output for a received input. Some neural networks include one or more hidden layers in addition to an output layer. The output of each hidden layer may be used as input to the next layer in the network, i.e., the next hidden layer or the output layer. Each layer of the network may generate an output from a received input in accordance with current values of a respective set of parameters. In the various embodiments, a reference to a "neural network" may be a reference to one or more neural networks.

A neural network may process information in two ways; when it is being trained it is in training mode and when it puts what it has learned into practice it is in inference (or prediction) mode. Neural networks may learn through a feedback process (e.g., backpropagation) which allows the network to adjust the weight factors (modifying its behavior) of the individual nodes in the intermediate hidden layers so that the output matches the outputs of the training data. In other words, a neural network learns by being provided with training data (learning examples) and eventually learns how to reach the correct output, even when it is presented with a new range or set of inputs. A neural network may include, for example, without limitation, at least one of a Feedforward Neural Network (FNN), a Recurrent Neural Network (RNN), a Modular Neural Network (MNN), a Convolutional Neural Network (CNN), a Residual Neural Network (ResNet), an Ordinary Differential Equations Neural Networks (neural-ODE), a Squeeze and Excitation embedded neural network, a MobileNet, or another type of neural network.

As used herein, "deep learning" may refer to the use of multi-layered artificial neural networks to automatically learn representations from input data such as images, video, text, etc., without human provided knowledge, to deliver highly accurate predictions in tasks such as object detection/ identification, speech recognition, language translation, etc.

As used herein, a "voxel" is a unit volume element (e.g., a volumetric pixel) of a regular grid of a three-dimensional entity with graphic information, such as a three-dimensional scan or image.

III. Automated Detection OF CNV

FIG. 1 is a block diagram of CNV evaluation system 100 in accordance with various embodiments. CNV evaluation system 100 is used to detect CNV activity, including, for example, a presence of the CNV disease or its progression over time, in the retinas of subjects. The CNV disease can be characterized by a complex and progressive disease, such as neovascular age-related macular degeneration (nAMD). The CNV activity may include growing of abnormal blood vessels originating in the choroid layer of the eye into the retina and leaking fluid from the blood into the retina. In such cases, the fluid that enters the retina may distort the vision of a subject and damage the retina itself, for example, by causing the loss of photoreceptors in the retina.

As illustrated in FIG. 1, CNV evaluation system 100 includes computing platform 102, data storage 104, and display system 106. Computing platform 102 may take various forms. In one or more embodiments, computing platform 102 includes a single computer (or computer system) or multiple computers in communication with each other. In other examples, computing platform 102 takes the form of a cloud computing platform, a mobile computing platform (e.g., a smartphone, a tablet, etc.), or a combination thereof.

Data storage 104 and display system 106 are each in communication with computing platform 102. In some examples, data storage 104, display system 106, or both may be considered part of or otherwise integrated with computing platform 102. Thus, in some examples, computing platform 102, data storage 104, and display system 106 may be separate components in communication with each other, but in other examples, some combination of these components may be integrated together.

As illustrated in FIG. 1, CNV evaluation system 100 includes image processor 108, which may be implemented using hardware, software, firmware, or a combination thereof. In one or more embodiments, image processor 108 is implemented in computing platform 102.

In various embodiments, a method for performing detection of CNV disease can be performed using CNV evaluation system 100, as described with respect to FIG. 1. The method can begin with inputting images for processing via CNV evaluation system 100 as follows. Image processor 108 receives image input 109 for processing. In one or more embodiments, image input 109 includes OCT imaging data 110 for a retina of a subject or a person. The OCT imaging data 110 may include, for example, one or more high-resolution OCT images of the retina. In one or more embodiments, image input 109 includes images generated by a same imaging device or from multiple devices. In various embodiments, the OCT imaging data 110 may include images of the same resolution or different resolutions, same size or different sizes (e.g., in terms of pixels), or same color depth or different color depths (e.g., 6-bit, 8-bit, 10-bit, 12-bit, etc.). In one or more embodiments, any image of the OCT imaging data 110 can be unregistered images. In other embodiments, any image of the OCT imaging data 110 may be registered images.

In various embodiments, image processor 108 processes image input 109 using a CNV detection system 112, to detect the presence of CNV in the retina of the subject. The CNV detection system 112 may employ machine learning with one or more neural networks based on the embodiments disclosed throughout the application. The one or more neural networks used in the disclosed method may include any number of or combination of neural networks. In one or more embodiments, CNV detection system 112 may include a convolutional neural network (CNN) system that includes one or more neural networks. In disclosed herein, one or more neural networks of the CNV detection system 112 may include, for example, without limitation, at least one of a Feedforward Neural Network (FNN), a Recurrent Neural Network (RNN), a Modular Neural Network (MNN), a Convolutional Neural Network (CNN), a Residual Neural Network (ResNet), an Ordinary Differential Equations Neural Networks (neural-ODE), a Squeeze and Excitation embedded neural network, a MobileNet, or another type of neural network. In various embodiments, one or more neural networks may be a deep learning neural network. In various embodiments, CNV detection system 112 may include at least one Squeeze and Excitation (SE) embedded neural network.

In one or more embodiments, image processor 108 generates output 114 that indicates whether the presence of CNV in the retina has been detected. For example, output 114 may be a probability value indicating the probability that CNV is present in the retina. The probability value can be anywhere from 0 to 100 and may be accompanied by a margin of error or an uncertainty number (e.g., plus or minus values). In some examples, output 114 may be a binary output that signals that CNV is present in the retina or that CNV is absent in the retina. In still other examples, output 114 may be a value indicating an amount of fluid associated with the retina that is detected from OCT imaging data 110. The value indicating the amount of fluid can be a numerical value, and/or may be accompanied by a measurement unit, such as, for example, nano-liter, micro-liter, etc. or any other suitable unit of measurements.

Figure 2:
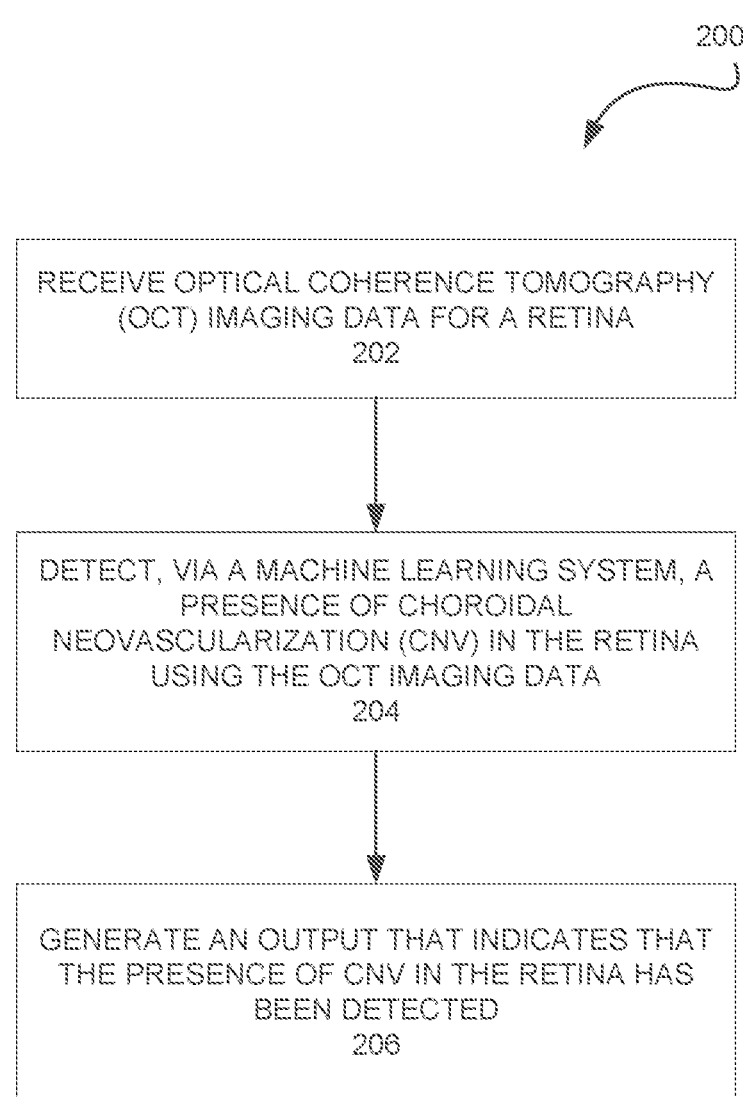
FIG. 2 is a flowchart of a process for detecting an advanced stage of age-related macular degeneration in a retina in accordance with various embodiments.

FIG. 2 is a flowchart of a process 200 for detecting an advanced stage of age-related macular degeneration in a retina in accordance with various embodiments. This advanced stage may be, for example, choroidal neovascularization (CNV). In various embodiments, process 200 is implemented using the CNV evaluation system 100 described with respect to FIG. 1.

As illustrated in FIG. 2, Step 202 includes receiving optical coherence tomography (OCT) imaging data for a retina of a patient. The OCT imaging data may include one or more OCT images, such as those described with respect to OCT imaging data 110 as described with respect to FIG. 1, and therefore, will not be described in further detail.

Step 204 includes detecting, via a machine learning system, a presence of choroidal neovascularization (CNV) in the retina using the OCT imaging data. In one or more embodiments, step 204 is performed by detecting a fluid associated with the retina. The fluid associated with the retina can include, for example, but not limited to, intraretinal fluid, subretinal fluid, and subretinal pigment epithelial fluid. The machine learning system used in detecting the presence of CNV may include, for example, a neural network system. The neural network system may take the form of a deep learning neural network system. In some embodiments, the neural network system may include one or more of a Feedforward Neural Network (FNN), a Recurrent Neural Network (RNN), a Modular Neural Network (MNN), a Convolutional Neural Network (CNN), a Residual Neural Network (ResNet), an Ordinary Differential Equations Neural Networks (neural-ODE), a Squeeze and Excitation embedded neural network, a MobileNet, or another type of neural network. In various embodiments, one or more neural networks may be a deep learning neural network. In various embodiments, one or more neural networks may include a Squeeze and Excitation (SE) embedded neural network.

In various embodiments, the neural network system may be trained on, for example, both CNV-positive OCT images and CNV-negative OCT images. In some embodiments, when the number of CNV-positive OCT images is different from the number of CNV-negative OCT images, the neural network model is trained with a weighted cross entropy loss function. The weighted cross entropy loss function can be used when adjusting model weights during training to minimize the loss between input and target. In various embodiments, the weighted cross entropy loss function is helpful in case of unbalanced dataset (positive vs. negative) since the model will pay more attention to the loss from the under-represented class.

Step 206 includes generating an output that indicates that the presence of CNV in the retina has been detected. This output, which may be output 114 in FIG. 1, may take various forms. For example, the output may be a probability value indicating the probability that CNV activity is present within the retina. The probability value can be a numerical value ranging between 0 and 100. The probability value may be accompanied by a margin of error or an uncertainty number. In various embodiments, the output is a binary output that signals whether CNV is present or absent in the retina. In various embodiments, step 206 may be implemented using the machine learning system as described in various embodiments of the disclosure.

Figure 3:
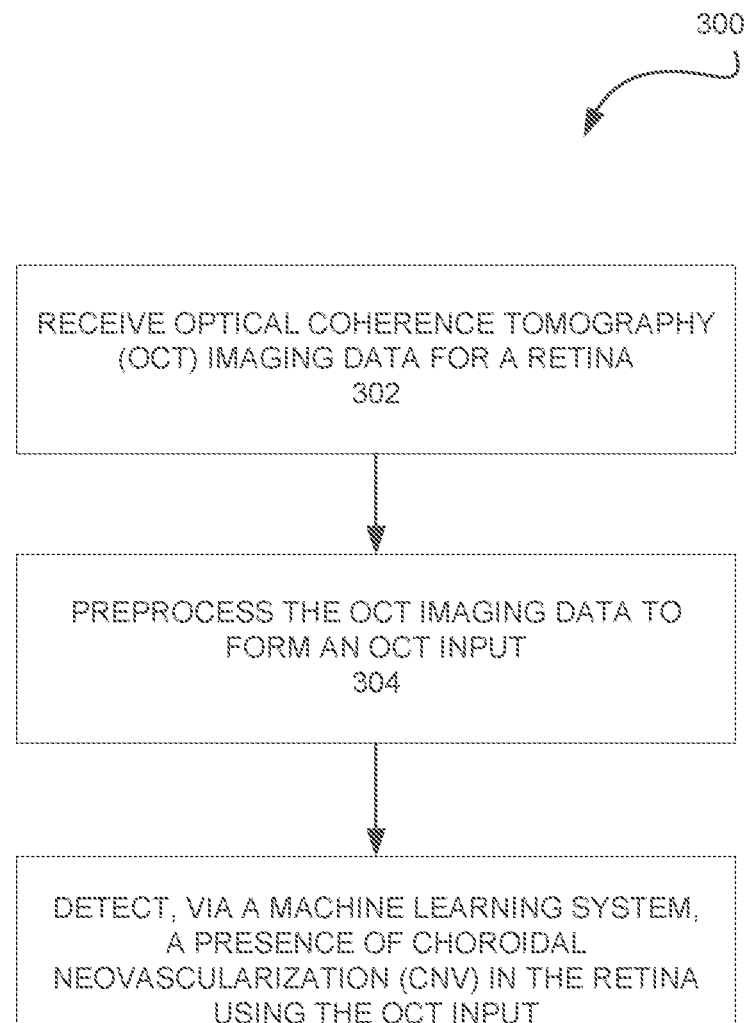
FIG. 3 is a flowchart of another process for detecting an advanced stage of age-related macular degeneration in a retina in accordance with various embodiments.

FIG. 3 is a flowchart of a process 300 for detecting an advanced stage of age-related macular degeneration in a retina in accordance with various embodiments. This advanced stage may be, for example, choroidal neovascularization (CNV). In various embodiments, process 300 is implemented using the CNV evaluation system 100 described with respect to FIG. 1.

Step 302 includes receiving optical coherence tomography (OCT) imaging data for a retina of a patient. The OCT imaging data may include one or more OCT images, such as those described with respect to OCT imaging data 110 as described with respect to FIG. 1, and therefore, will not be described in further detail.

Once the OCT imaging data is received, process 300 proceeds to step 304, which includes preprocessing the OCT imaging data to form an OCT input. In some embodiments, the preprocessing of the OCT imaging data may include selecting a portion of the OCT imaging data that captures a retinal pigment epithelium (RPE) layer of the retina as the OCT input. As one example, the preprocessing may include flattening an OCT image towards the RPE layer of the retina and selecting a portion of the OCT image that includes the RPE layer of the retina, a first area above the RPE layer, and/or a second area below the RPE layer.

Step 306 includes detecting, via a machine learning system, a presence of choroidal neovascularization (CNV) in the retina using the OCT input. The machine learning system used in detecting the presence of CNV may include, for example, a neural network system. The neural network system may take the form of a deep learning neural network system. In some embodiments, the neural network system may include one or more of a Feedforward Neural Network (FNN), a Recurrent Neural Network (RNN), a Modular Neural Network (MNN), a Convolutional Neural Network (CNN), a Residual Neural Network (ResNet), an Ordinary Differential Equations Neural Networks (neural-ODE), a Squeeze and Excitation embedded neural network, a MobileNet, or another type of neural network. In various embodiments, one or more neural networks may be a deep learning neural network. In various embodiments, one or more neural networks may include a Squeeze and Excitation (SE) embedded neural network.

In one or more embodiments, the machine learning system includes a neural network system that is trained to detect fluid in the retina, with the presence of the fluid indicating the presence of CNV. The fluid may include, for example, but is not limited to, intraretinal fluid, subretinal fluid, subretinal pigment epithelial fluid, or a combination thereof.

In one or more embodiments, an output may be generated based on the detection of the presence of CNV in step 306. This output, which is the same or substantially similar to output 114 in FIG. 1, may take various forms. For example, the output may be a probability value indicating the probability that CNV activity is present within the retina. The probability value can be a numerical value ranging between 0 and 100. The probability value may be accompanied by a margin of error or an uncertainty number. In various embodiments, the output is a binary output that signals whether CNV is present or absent in the retina.

Figure 4:
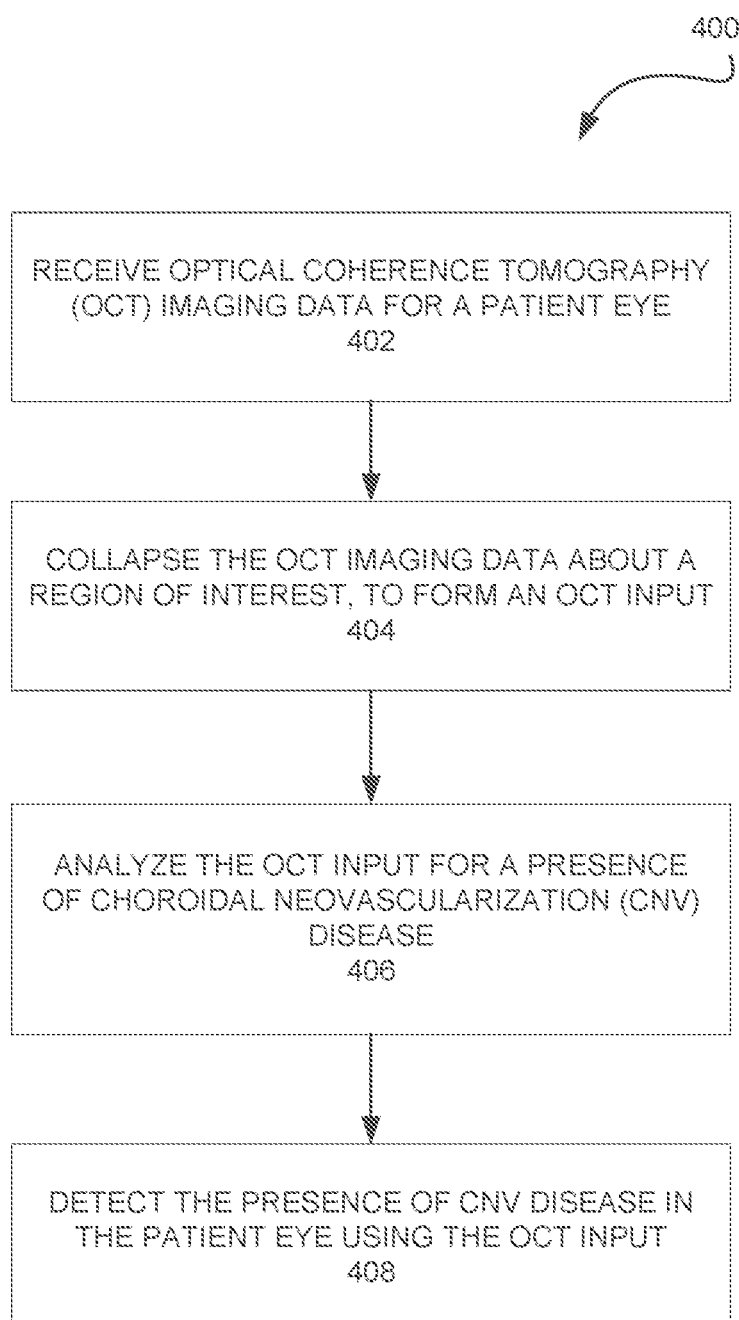
FIG. 4 is a flowchart of another process for detecting an advanced stage of age-related macular degeneration in a retina in accordance with various embodiments.

FIG. 4 is a flowchart of an example process 400 in accordance with various embodiments. Process 400 can be used for detecting an advanced stage of age-related macular degeneration in a retina in accordance with various embodiments. This advanced stage may be, for example, choroidal neovascularization (CNV). In various embodiments, process 400 is implemented using the CNV evaluation system 100 described with respect to FIG. 1.

As illustrated, step 402 of process 400 includes receiving OCT imaging data for a patient eye. The OCT imaging data may include one or more OCT images, such as those described with respect to OCT imaging data 110 as described with respect to FIG. 1.

Once the OCT imaging data is received, process 400 proceeds to step 404, which includes collapsing the OCT imaging data about a region of interest, to form an OCT input. In various embodiments, collapsing the OCT imaging data includes collapsing the OCT imaging data about a retinal pigment epithelium (RPE) layer of the patient eye, to form the OCT input. In various embodiments, collapsing the OCT imaging data includes flattening one or more OCT images of the OCT imaging data towards the RPE layer. In various embodiments, collapsing the OCT imaging data includes cropping a number of pixels about the RPE layer.

As illustrated in FIG. 4, process 400 proceeds to step 406, which includes analyzing the OCT input for a presence of choroidal neovascularization (CNV) disease.

Once the OCT input is analyzed, process 400 proceeds to step 408, which includes detecting the presence of CNV disease in the patient eye using the OCT input. In various embodiments, detecting the presence of CNV disease includes detecting retinal fluid in the patient eye using the OCT input, wherein the retinal fluid comprises at least one of intraretinal fluid, subretinal fluid, or subretinal pigment epithelial fluid.

In various embodiments, detecting the presence of CNV disease in the patient eye is performed using a machine learning system. In some embodiments, detecting the presence of CNV disease is performed using a machine learning system including a recalibration module. In some implementations, detecting the presence of CNV disease is performed via a squeeze and excitation module embedded on a machine learning system. In various implementations, the machine learning system used in detecting the presence of CNV may include, for example, a neural network system. The neural network system may take the form of a deep learning neural network system. In some embodiments, the neural network system may include one or more of a Feedforward Neural Network (FNN), a Recurrent Neural Network (RNN), a Modular Neural Network (MNN), a Convolutional Neural Network (CNN), a Residual Neural Network (ResNet), an Ordinary Differential Equations Neural Networks (neural-ODE), a Squeeze and Excitation embedded neural network, a MobileNet, or another type of neural network. In various embodiments, one or more neural networks may be a deep learning neural network. In various embodiments, one or more neural networks may include a Squeeze and Excitation (SE) embedded neural network.

In one or more embodiments, the machine learning system includes a neural network system that is trained to detect fluid in the retina, with the presence of the fluid indicating the presence of CNV. The fluid may include, for example, but is not limited to, intraretinal fluid, subretinal fluid, subretinal pigment epithelial fluid, or a combination thereof.

In one or more embodiments, an output may be generated based on the detection of the presence of CNV in step 408. This output generated based on the detection in step 408 is the same or substantially similar to output 114 in FIG. 1, and thus may take various forms. In some embodiments, the output may be a probability value indicating the probability that CNV activity is present within the retina. The probability value can be a numerical value ranging between 0 and 100. The probability value may be accompanied by a margin of error or an uncertainty number. In various embodiments, the output is a binary output that signals whether CNV is present or absent in the patient eye or retina of the patient eye.

Figure 5:
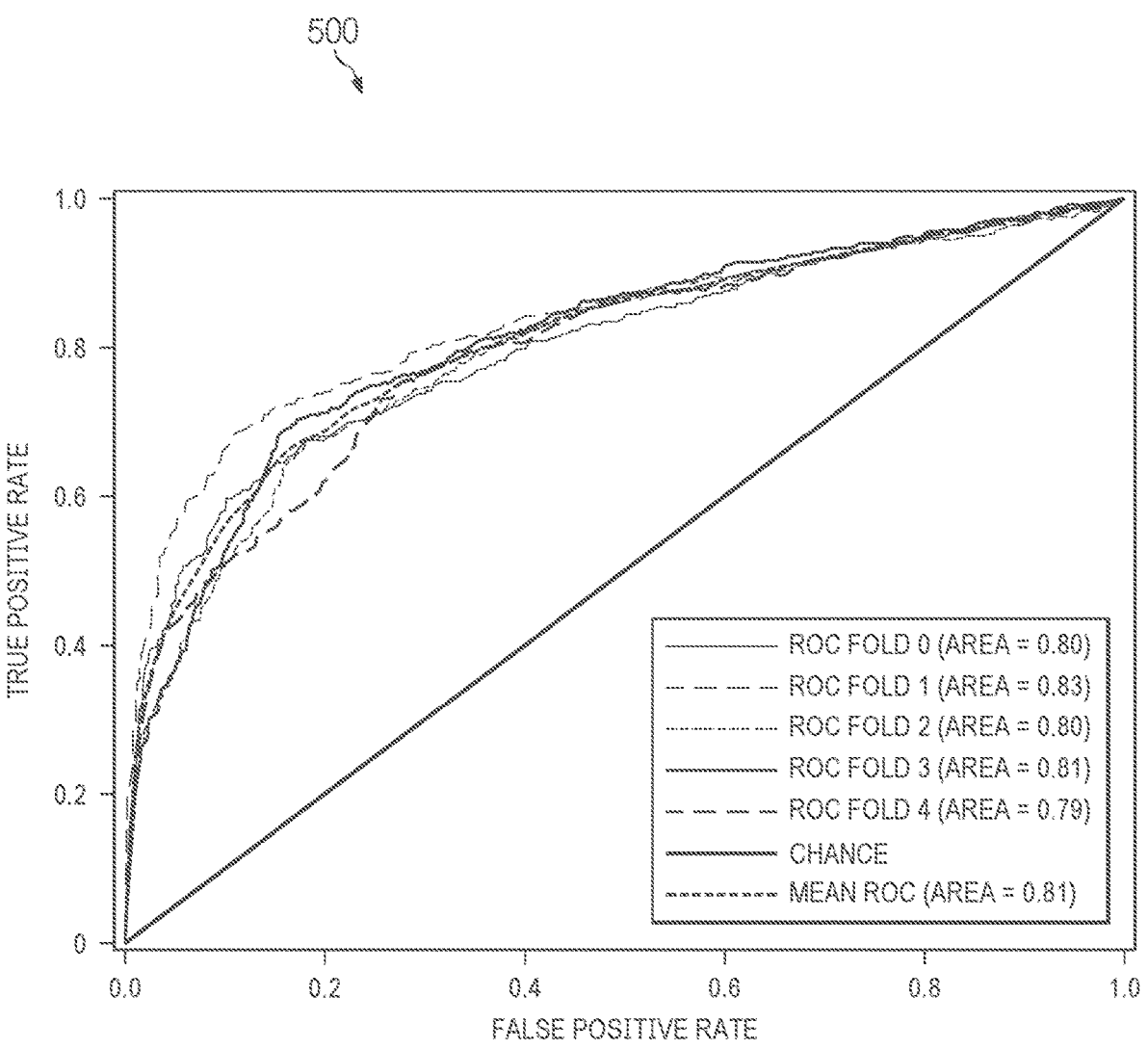
FIG. 5 is a plot displaying a number of receiver operating curves (ROCs) based on a large number of test images from a number of subjects using the CNV detection system of FIG. 1.

FIG. 5 is a plot 500 displaying a number of receiver operating curves (ROCs) based on a large number of test images from a number of subjects using a CNV detection method or system such as, for example, the CNV evaluation system 100 of FIG. 1. The plot 500 demonstrates that a deep learning (DL) neural network (DL model with DL algorithms), such as that used in the CNV detection system of FIG. 1, can accurately detect a CNV disease activity based on changes in the retinal anatomy on OCT imaging data, for example OCT imaging data 110. Although the DL neural network in generating the curves displayed in the plot 500, other neural networks as described with respect to CNV detection system 112 can be used to generate the same or similar curves displayed in the plot 500. The DL model is evaluated on a test set of 1,706 images from 102 subjects and achieved an Area Under Receiver Operating Curve (AU-ROC) of 0.81±0.012, with accuracy of 0.76±0.027, sensitivity of 0.66±0.028, and specificity of 0.83±0.029.

In generating the plot 500 of FIG. 5, a total of 8,527 OCT images are evaluated. The OCT images are obtained from the pro re nata (PRN) arms of the HARBOR trial (clinical trial registration number: NCT00891735) that evaluated ranibizumab in neovascular age-related macular degeneration (nAMD). Disease activity, for example, a presence or an absence of CNV disease, in the study eye can be defined as fluid on OCT (e.g., intra-retinal fluid, subretinal fluid, or subretinal pigment epithelial fluid) or if a subject's visual acuity decreased ≥5 letters from the previous visit. In some instances, disease activity can also be defined solely by the presence of retinal fluid associated with underlying CNV on OCT without the requirement of a decrease of ≥5 letters relative to the previous visit. In this subset of visits, study eye OCT scans of 1024×512×128 voxels are collected from Zeiss Cirrus machine and are flattened towards the retinal pigment epithelium (RPE) layer, and cropped to 384 pixels above and 128 below RPE. To accommodate the graphical processing unit (GPU) memory constraints of the computer system used for the study, the central 15 B-scans are selected as representatives. As such, the input size of each scan to the network is 512×512×15. A total of 8,527 scans from 521 subjects are used. 3,618 of them are from diseased eyes and 4,909 are without disease. They are split into training and test sets in a 4:1 ratio using stratified sampling. Five-fold cross validation is applied only using training set to optimize parameters. A Squeeze and Excitation (SE) embedded neural network model (with MobileNet) is designed to classify eyes with and without CNV disease. MobileNet greatly reduces a model size using depth-wise separable convolutions and SE module contributes by adaptively recalibrating channel-wise feature response. Weighted cross entropy is used as a loss function since the number of samples in each class are unbalanced. In some instances, data augmentation, including rotation, translation, and/or flipping is applied during training of the model/neural network.

In accordance with various embodiments disclosed herein, a method for detecting a choroidal neovascularization (CNV) disease is described. In various embodiments, various process steps of the method can be performed using a system, such as CNV evaluation system 100 of FIG. 1. The method includes receiving optical coherence tomography (OCT) imaging data for a patient eye; collapsing the OCT imaging data about a region of interest, to form an OCT input; analyzing the OCT input for a presence of choroidal neovascularization (CNV) disease; and detecting the presence of CNV disease in the patient eye using the OCT input.

In various embodiments of the method, detecting the presence of CNV disease comprises detecting retinal fluid in the patient eye using the OCT input, wherein the retinal fluid comprises at least one of intraretinal fluid, subretinal fluid, or subretinal pigment epithelial fluid.

In various embodiments of the method, collapsing the OCT imaging data comprises collapsing the OCT imaging data about a retinal pigment epithelium (RPE) layer of the patient eye, to form the OCT input. In various embodiments, collapsing the OCT imaging data comprises flattening one or more OCT images of the OCT imaging data towards the RPE layer. In various embodiments, collapsing the OCT imaging data comprises cropping a number of pixels about the RPE layer.

In various embodiments of the method, the detecting the presence of CNV disease is performed using a machine learning system including a recalibration module. In various embodiments, the detecting the presence of CNV disease is performed via a squeeze and excitation module embedded on a machine learning system.

In accordance with various embodiments disclosed herein, automated detection of choroidal neovascularization (CNV) disease can be performed an example system, such as CNV evaluation system 100 as described with respect to FIG. 1. In various embodiments, the system includes a non-transitory memory; and a hardware processor coupled with the non-transitory memory and configured to read instructions from the non-transitory memory to cause the system to perform operations. For example, CNV evaluation system 100 can be used to receive optical coherence tomography (OCT) imaging data, such as OCT imaging data 110, for a patient eye. Further, CNV evaluation system 100 of FIG. 1 can be used for processing. For example, image processor 108 of CNV evaluation system 100 can be used to process image input 109 using a machine learning system, such as CNV detection system 112. Some non-limiting examples of processing may include collapsing the OCT imaging data about a region of interest, to form an OCT input.

In various embodiments, a neural network system, such as CNV detection system 112 of CNV evaluation system 100, may be used for analyzing the OCT input for a presence of CNV disease and/or detecting the presence of CNV disease in the patient eye using the OCT input. The neural network system used in analyzing the OCT input may include any number of or combination of neural networks. In some embodiments, the neural network system may take the form of a convolutional neural network system that includes one or more neural networks. In some embodiments, neural network system may include any of a Feedforward Neural Network (FNN), a Recurrent Neural Network (RNN), a Modular Neural Network (MNN), a Convolutional Neural Network (CNN), a Residual Neural Network (ResNet), an Ordinary Differential Equations Neural Networks (neural-ODE), a Squeeze and Excitation embedded neural network, a MobileNet, or another type of neural network. In various embodiments, the neural network system may be a deep learning neural network or Squeeze and Excitation (SE) embedded neural network.

In various embodiments of the system, detecting the presence of CNV disease comprises detecting retinal fluid in the patient eye using the OCT input, wherein the retinal fluid comprises at least one of intraretinal fluid, subretinal fluid, or subretinal pigment epithelial fluid. In various embodiments of the system, collapsing the OCT imaging data comprises collapsing the OCT imaging data about the patient's retinal pigment epithelium (RPE) layer, to form the OCT input. In various embodiments of the system, collapsing the OCT imaging data comprises flattening OCT images of the OCT imaging data towards the RPE layer. In various embodiments of the system, collapsing the OCT imaging data comprises cropping a number of pixels about the RPE layer.

In various embodiments of the system, the machine learning system used for detecting the presence of CNV disease may include a recalibration module. In various embodiments, the detecting the presence of CNV disease is performed via a squeeze and excitation module embedded on a machine learning system.

In accordance with various embodiments disclosed herein, a non-transitory computer-readable medium having stored thereon computer-readable instructions is described. The non-transitory computer-readable medium includes computer-readable instructions executable to cause a computer system to perform operations. In various embodiments, the operations can be performed using a CNV detection system such as, for example, CNV evaluation system 100 as described with respect to FIG. 1. The computer-readable instructions of the operations includes: receiving optical coherence tomography (OCT) imaging data for a patient eye; collapsing the OCT imaging data about a region of interest, to form an OCT input; analyzing the OCT input for a presence of CNV disease; and detecting the presence of CNV disease in the patient eye using the OCT input.

In various embodiments, detecting the presence of CNV disease comprises detecting retinal fluid in the patient eye using the OCT input, wherein the retinal fluid comprises at least one of intraretinal fluid, subretinal fluid, or subretinal pigment epithelial fluid.

In various embodiments, collapsing the OCT imaging data includes collapsing the OCT imaging data about the patient's retinal pigment epithelium (RPE) layer, to form the OCT input. In various embodiments, collapsing the OCT imaging data comprises flattening OCT images of the OCT imaging data towards the RPE layer. In various embodiments, collapsing the OCT imaging data comprises cropping a number of pixels about the RPE layer. In various embodiments, the detecting the presence of CNV disease is performed via a squeeze and excitation module embedded on a machine learning system.

IV. Computer Implemented System

Figure 6:
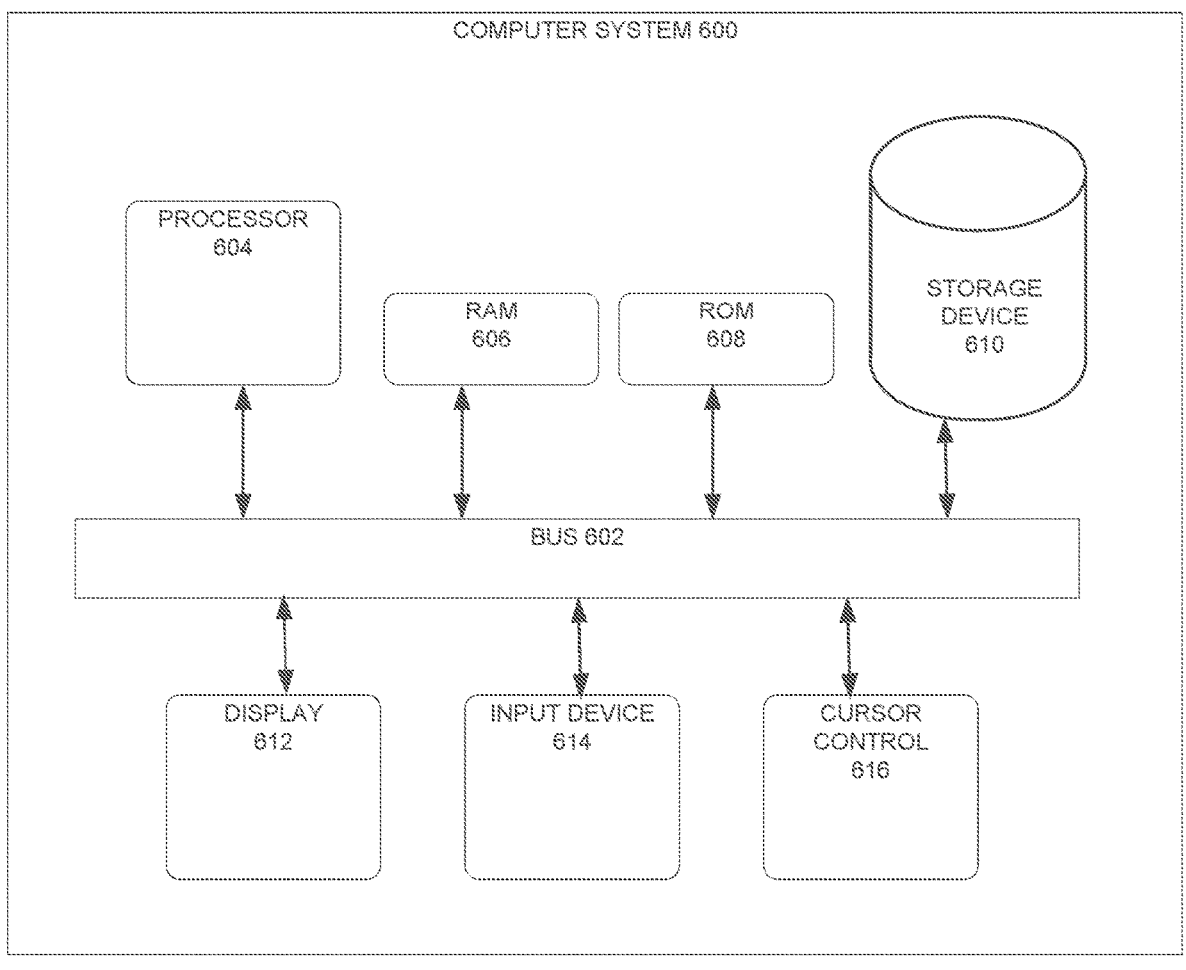
FIG. 6 is a block diagram of a computer system in accordance with various embodiments.

FIG. 6 is a block diagram of a computer system in accordance with various embodiments. Computer system 600 may be an example of one implementation for computing platform 102 described above in FIG. 1. In one or more examples, computer system 600 can include a bus 602 or other communication mechanism for communicating information, and a processor 604 coupled with bus 602 for processing information. In various embodiments, computer system 600 can also include a memory, which can be a random-access memory (RAM) 606 or other dynamic storage device, coupled to bus 602 for determining instructions to be executed by processor 604. Memory also can be used for storing temporary variables or other intermediate information during execution of instructions to be executed by processor 604. In various embodiments, computer system 600 can further include a read only memory (ROM) 608 or other static storage device coupled to bus 602 for storing static information and instructions for processor 604. A storage device 610, such as a magnetic disk or optical disk, can be provided and coupled to bus 602 for storing information and instructions.

In various embodiments, computer system 600 can be coupled via bus 602 to a display 612, such as a cathode ray tube (CRT) or liquid crystal display (LCD), for displaying information to a computer user. An input device 614, including alphanumeric and other keys, can be coupled to bus 602 for communicating information and command selections to processor 604. Another type of user input device is a cursor control 616, such as a mouse, a joystick, a trackball, a gesture input device, a gaze-based input device, or cursor direction keys for communicating direction information and command selections to processor 604 and for controlling cursor movement on display 612. This input device 614 typically has two degrees of freedom in two axes, a first axis (e.g., x) and a second axis (e.g., y), that allows the device to specify positions in a plane. However, it should be understood that input devices 614 allowing for three-dimensional (e.g., x, y and z) cursor movement are also contemplated herein.

Consistent with certain implementations of the present teachings, results can be provided by computer system 600 in response to processor 604 executing one or more sequences of one or more instructions contained in RAM 606. Such instructions can be read into RAM 606 from another computer-readable medium or computer-readable storage medium, such as storage device 610. Execution of the sequences of instructions contained in RAM 606 can cause processor 604 to perform the processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, storage device, data storage device, etc.) or "computer-readable storage medium" as used herein refers to any media that participates in providing instructions to processor 604 for execution. Such a medium can take many forms, including but not limited to, non-volatile media, volatile media, and transmission media. Examples of non-volatile media can include, but are not limited to, optical, solid state, magnetic disks, such as storage device 610. Examples of volatile media can include, but are not limited to, dynamic memory, such as RAM 606. Examples of transmission media can include, but are not limited to, coaxial cables, copper wire, and fiber optics, including the wires that comprise bus 602.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 604 of computer system 600 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, optical communications connections, etc.

It should be appreciated that the methodologies described herein, flow charts, diagrams, and accompanying disclosure can be implemented using computer system 600 as a stand-alone device or on a distributed network of shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 600, whereby processor 604 would execute the analyses and determinations provided by these engines, subject to instructions provided by any one of, or a combination of, the memory components RAM 606, ROM, 608, or storage device 610 and user input provided via input device 614.

V. Artificial Neural Networks

Figure 7:
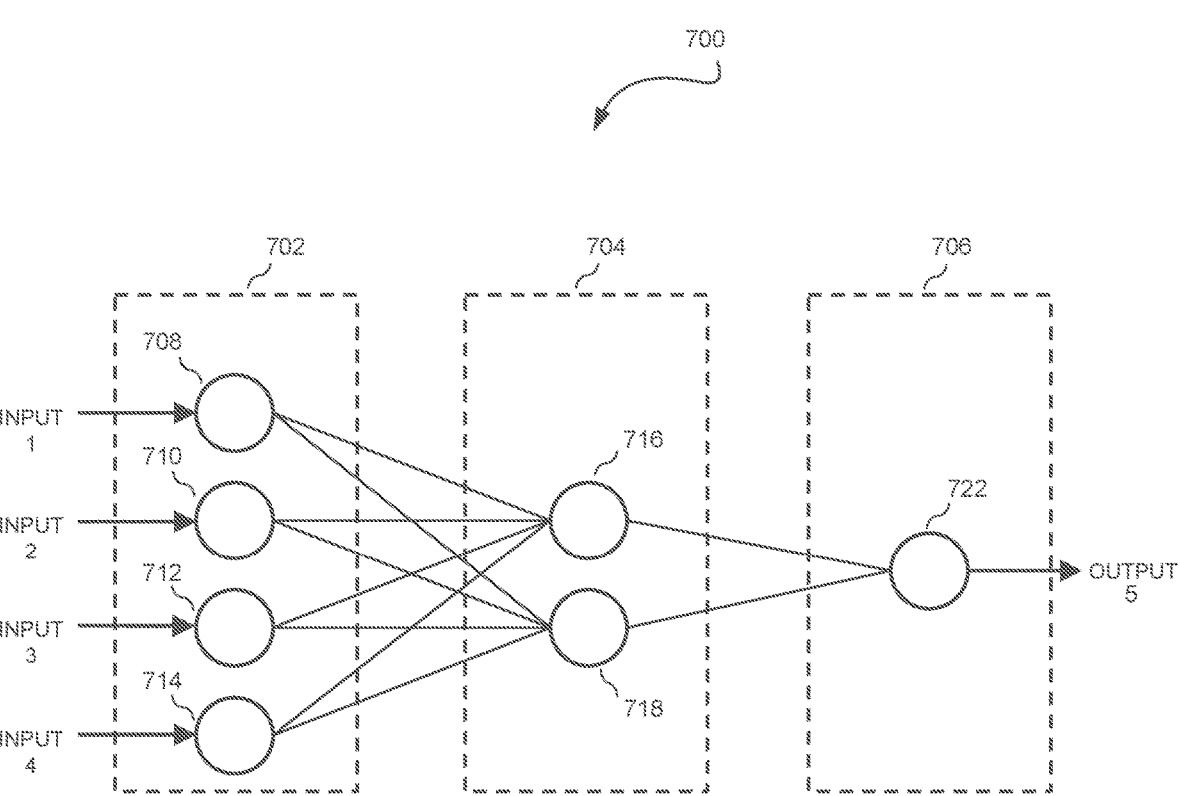
FIG. 7 illustrates an example neural network that can be used to implement a deep learning neural network in accordance with various embodiments.

FIG. 7 illustrates an example neural network that can be used to implement a computer-based model according to various embodiments of the present disclosure. For example, the neural network 700 may be used to implement the CNV detection system 112 of the CNV evaluation system 100. As shown, the artificial neural network 700 includes three layers—an input layer 702, a hidden layer 704, and an output layer 706. Each of the layers 702, 704, and 706 may include one or more nodes. For example, the input layer 702 includes nodes 708-714, the hidden layer 704 includes nodes 716-718, and the output layer 706 includes a node 722. In this example, each node in a layer is connected to every node in an adjacent layer. For example, the node 708 in the input layer 702 is connected to both of the nodes 716, 718 in the hidden layer 704. Similarly, the node 716 in the hidden layer is connected to all of the nodes 708-714 in the input layer 702 and the node 722 in the output layer 706. Although only one hidden layer is shown for the artificial neural network 700, it has been contemplated that the artificial neural network 700 used to implement a neural network system, such as the CNV detection system 112 of the CNV evaluation system 100, may include as many hidden layers as necessary or desired.

In this example, the artificial neural network 700 receives a set of input values (inputs 1-4) and produces an output value (output 5). Each node in the input layer 702 may correspond to a distinct input value. For example, when the artificial neural network 700 is used to implement a neural network system, such as the CNV detection system 112 of the CNV evaluation system 100, each node in the input layer 702 may correspond to a distinct attribute of the OCT imaging data 110.

In some embodiments, each of the nodes 716-718 in the hidden layer 704 generates a representation, which may include a mathematical computation (or algorithm) that produces a value based on the input values received from the nodes 708-714. The mathematical computation may include assigning different weights to each of the data values received from the nodes 708-714. The nodes 716 and 718 may include different algorithms and/or different weights assigned to the data variables from the nodes 708-714 such that each of the nodes 716-718 may produce a different value based on the same input values received from the nodes 708-714. In some embodiments, the weights that are initially assigned to the features (or input values) for each of the nodes 716-718 may be randomly generated (e.g., using a computer randomizer). The values generated by the nodes 716 and 718 may be used by the node 722 in the output layer 706 to produce an output value for the artificial neural network 700. When the artificial neural network 700 is used to implement a neural network system, such as the CNV detection system 112 of the CNV evaluation system 100, the output value produced by the artificial neural network 700 may include the output 114.

The artificial neural network 700 may be trained by using training data. For example, the training data herein may be a set of images from OCT imaging data 110. By providing training data to the artificial neural network 700, the nodes 716-718 in the hidden layer 704 may be trained (adjusted) such that an optimal output is produced in the output layer 706 based on the training data. By continuously providing different sets of training data, and penalizing the artificial neural network 700 when the output of the artificial neural network 700 is incorrect (e.g., when generating segmentation masks including incorrect GA lesion segments), the artificial neural network 700 (and specifically, the representations of the nodes in the hidden layer 704) may be trained (adjusted) to improve its performance in data classification. Adjusting the artificial neural network 700 may include adjusting the weights associated with each node in the hidden layer 704.

Although the above discussions pertain to an artificial neural network as an example of machine learning, it is understood that other types of machine learning methods may also be suitable to implement the various aspects of the present disclosure. For example, support vector machines (SVMs) may be used to implement machine learning. SVMs are a set of related supervised learning methods used for classification and regression. A SVM training algorithm—which may be a non-probabilistic binary linear classifier—may build a model that predicts whether a new example falls into one category or another. As another example, Bayesian networks may be used to implement machine learning. A Bayesian network is an acyclic probabilistic graphical model that represents a set of random variables and their conditional independence with a directed acyclic graph (DAG). The Bayesian network could present the probabilistic relationship between one variable and another variable. Another example is a machine learning engine that employs a decision tree learning model to conduct the machine learning process. In some instances, decision tree learning models may include classification tree models, as well as regression tree models. In some embodiments, the machine learning engine employs a Gradient Boosting Machine (GBM) model (e.g., XGBoost) as a regression tree model. Other machine learning techniques may be used to implement the machine learning engine, for example via Random Forest or Deep Neural Networks. Other types of machine learning algorithms are not discussed in detail herein for reasons of simplicity and it is understood that the present disclosure is not limited to a particular type of machine learning.

VI. Conclusion

While the present teachings are described in conjunction with various embodiments, it is not intended that the present teachings be limited to such embodiments. On the contrary, the present teachings encompass various alternatives, modifications, and equivalents, as will be appreciated by those of skill in the art.

For example, the flowcharts and block diagrams described above illustrate the architecture, functionality, and/or operation of possible implementations of various method and system embodiments. Each block in the flowcharts or block diagrams may represent a module, a segment, a function, a portion of an operation or step, or a combination thereof. In some alternative implementations of an embodiment, the function or functions noted in the blocks may occur out of the order noted in the figures. For example, in some cases, two blocks shown in succession may be executed substantially concurrently. In other cases, the blocks may be performed in the reverse order. Further, in some cases, one or more blocks may be added to replace or supplement one or more other blocks in a flowchart or block diagram.

Thus, in describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

VII. Recitation of Embodiments

Embodiment 1: A method comprising: receiving optical coherence tomography (OCT) imaging data for a patient eye; collapsing the OCT imaging data about a region of interest, to form an OCT input; analyzing the OCT input for a presence of choroidal neovascularization (CNV) disease; and detecting the presence of CNV disease in the patient eye using the OCT input.

Embodiment 2: The method of Embodiment 1, wherein detecting the presence of CNV disease comprises detecting retinal fluid in the patient eye using the OCT input, wherein the retinal fluid comprises at least one of intraretinal fluid, subretinal fluid, or subretinal pigment epithelial fluid.

Embodiment 3: The method of Embodiments 1 or 2, wherein collapsing the OCT imaging data comprises collapsing the OCT imaging data about a retinal pigment epithelium (RPE) layer of the patient eye, to form the OCT input.

Embodiment 4: The method of Embodiment 3, wherein collapsing the OCT imaging data comprises flattening one or more OCT images of the OCT imaging data towards the RPE layer.

Embodiment 5: The method of Embodiments 3 or 4, wherein collapsing the OCT imaging data comprises cropping a number of pixels about the RPE layer.

Embodiment 6: The method of any of Embodiments 1-5, wherein the detecting the presence of CNV disease is performed using a machine learning system including a recalibration module.

Embodiment 7: The method of any of Embodiments 1-6, wherein the detecting the presence of CNV disease is performed via a squeeze and excitation module embedded on a machine learning system.

Embodiment 8: A system, comprising: a non-transitory memory; and a hardware processor coupled with the non-transitory memory and configured to read instructions from the non-transitory memory to cause the system to perform operations comprising: receiving optical coherence tomography (OCT) imaging data for a patient eye; collapsing the OCT imaging data about a region of interest, to form an OCT input; analyzing the OCT input for a presence of CNV disease; and detecting the presence of CNV disease in the patient eye using the OCT input.

Embodiment 9: The system of Embodiment 8, wherein detecting the presence of CNV disease comprises detecting retinal fluid in the patient eye using the OCT input, wherein the retinal fluid comprises at least one of intraretinal fluid, subretinal fluid, or subretinal pigment epithelial fluid.

Embodiment 10: The system of Embodiments 8 or 9, wherein collapsing the OCT imaging data comprises collapsing the OCT imaging data about the patient's retinal pigment epithelium (RPE) layer, to form the OCT input.

Embodiment 11: The system of Embodiment 10, wherein collapsing the OCT imaging data comprises flattening OCT images of the OCT imaging data towards the RPE layer.

Embodiment 12: The system of Embodiments 10 or 11, wherein collapsing the OCT imaging data comprises cropping a number of pixels about the RPE layer.

Embodiment 13: The system of any of Embodiments 8-12, wherein the detecting the presence of CNV disease is performed using a machine learning system including a recalibration module.

Embodiment 14: The system of any of Embodiments 8-13, wherein the detecting the presence of CNV disease is performed via a squeeze and excitation module embedded on a machine learning system.

Embodiment 15: A non-transitory computer-readable medium having stored thereon computer-readable instructions executable to cause a computer system to perform operations comprising: receiving optical coherence tomography (OCT) imaging data for a patient eye; collapsing the OCT imaging data about a region of interest, to form an OCT input; analyzing the OCT input for a presence of CNV disease; and detecting the presence of CNV disease in the patient eye using the OCT input.

Embodiment 16: The non-transitory computer-readable medium of Embodiment 15, wherein detecting the presence of CNV disease comprises detecting retinal fluid in the patient eye using the OCT input, wherein the retinal fluid comprises at least one of intraretinal fluid, subretinal fluid, or subretinal pigment epithelial fluid.

Embodiment 17: The non-transitory computer-readable medium of Embodiments 15 or 16, wherein collapsing the OCT imaging data comprises collapsing the OCT imaging data about the patient's retinal pigment epithelium (RPE) layer, to form the OCT input.

Embodiment 18: The non-transitory computer-readable medium of Embodiment 17, wherein collapsing the OCT imaging data comprises flattening OCT images of the OCT imaging data towards the RPE layer.

Embodiment 19: The non-transitory computer-readable medium of any of Embodiments 15-18, wherein collapsing the OCT imaging data comprises cropping a number of pixels about the RPE layer.

Embodiment 20: The non-transitory computer-readable medium of any of Embodiments 15-19, wherein the detecting the presence of CNV disease is performed via a squeeze and excitation module embedded on a machine learning system.

The invention claimed is:

1. A method comprising:
receiving optical coherence tomography (OCT) imaging data for a patient eye;
collapsing the OCT imaging data about a region of interest, to form an OCT input, comprising:
flattening one or more OCT images of the OCT imaging data about a retinal pigment epithelium (RPE) layer of the patient eye;
cropping a number of pixels about the RPE layer;
wherein cropping the number of pixels about the RPE layer comprises cropping a first number of pixels above the RPE layer and a second number of pixels below the RPE layer; and
selecting a predetermined number of central B-scans as the OCT input;
analyzing the OCT input for a presence of choroidal neovascularization (CNV) disease; and
generating an output that indicates the detection of the presence of CNV disease in the patient eye using the OCT input;
wherein the output comprises a margin of error or an uncertainty number.

2. The method of claim 1, wherein detecting the presence of CNV disease comprises detecting retinal fluid in the patient eye using the OCT input, wherein the retinal fluid comprises at least one of intraretinal fluid, subretinal fluid, or subretinal pigment epithelial fluid.

3. The method of claim 2, wherein the output further comprises a value indicating the amount of retinal fluid in the patient eye.

4. The method of claim 1, wherein the detecting the presence of CNV disease is performed using a machine learning system including a recalibration module.

5. The method of claim 1, wherein the detecting the presence of CNV disease is performed via a squeeze and excitation module embedded on a machine learning system.

6. The method of claim 1, wherein the predetermined number of central B-scans is less than 30.

7. The method of claim 1, wherein the output comprises a probability value indicating the probability of the presence of CNV disease.

8. The method of claim 1, wherein the first number of pixels is more than twice the second number of pixels.

9. The method of claim 1, wherein the first number of pixels is three times more than the second number of pixels.

10. A system, comprising:

a non-transitory memory; and a hardware processor coupled with the non-transitory memory and configured to read instructions from the non-transitory memory to cause the system to perform operations comprising:

receiving optical coherence tomography (OCT) imaging data for a patient eye;

collapsing the OCT imaging data about a region of interest, to form an OCT input, comprising:

flattening one or more OCT images of the OCT imaging data about a retinal pigment epithelium (RPE) layer of the patient eye;

cropping a number of pixels about the RPE layer;

wherein cropping the number of pixels about the RPE layer comprises cropping a first number of pixels above the RPE layer and a second number of pixels below the RPE layer; and selecting a predetermined number of central B-scans as the OCT input;

analyzing the OCT input for a presence of CNV disease; and generating an output that indicates the detection of the presence of CNV disease in the patient eye using the OCT input;

wherein the output comprises a probability value indicating the probability of the presence of CNV disease and a margin of error or an uncertainty number.

11. The system of claim 10, wherein detecting the presence of CNV disease comprises detecting retinal fluid in the patient eye using the OCT input, wherein the retinal fluid comprises at least one of intraretinal fluid, subretinal fluid, or subretinal pigment epithelial fluid.

12. The system of claim 10, wherein the detecting the presence of CNV disease is performed using a machine learning system including a recalibration module.

13. The system of claim 10, wherein the detecting the presence of CNV disease is performed via a squeeze and excitation module embedded on a machine learning system.

14. The system of claim 10, wherein the first number of pixels is more than twice the second number of pixels.

15. The system of claim 10, wherein the first number of pixels is three times more than the second number of pixels.

16. A non-transitory computer-readable medium having stored thereon computer-readable instructions executable to cause a computer system to perform operations comprising:

receiving optical coherence tomography (OCT) imaging data for a patient eye;

collapsing the OCT imaging data about a region of interest, to form an OCT input comprising:

flattening one or more OCT images of the OCT imaging data about a retinal pigment epithelium (RPE) layer of the patient eye;

cropping a number of pixels about the RPE layer;

wherein cropping the number of pixels about the RPE layer comprises cropping a first number of pixels above the RPE layer and a second number of pixels below the RPE layer; and selecting a predetermined number of central B-scans as the OCT input;

analyzing the OCT input for a presence of CNV disease; and generating an output that indicates the detection of the presence of CNV disease in the patient eye using the OCT input;

wherein the output comprises a probability value indicating the probability of the presence of CNV disease and a margin of error or an uncertainty number.

17. The non-transitory computer-readable medium of claim 16, wherein detecting the presence of CNV disease comprises detecting retinal fluid in the patient eye using the OCT input, wherein the retinal fluid comprises at least one of intraretinal fluid, subretinal fluid, or subretinal pigment epithelial fluid.

18. The non-transitory computer-readable medium of claim 16, wherein the detecting the presence of CNV disease is performed via a squeeze and excitation module embedded on a machine learning system.

19. The non-transitory computer-readable medium of claim 16, wherein the first number of pixels is more than twice the second number of pixels.

20. The non-transitory computer-readable medium of claim 16, wherein the first number of pixels is three times more than the second number of pixels.

* * * * *